United States Patent
Wyrzykiewicz et al.

(10) Patent No.: US 8,513,404 B2
(45) Date of Patent: Aug. 20, 2013

(54) PROCESS FOR THE MANUFACTURE OF OLIGONUCLEOTIDES

(75) Inventors: Tadeusz Krzysztof Wyrzykiewicz, Wyoming, OH (US); Hagen Cramer, West Chester, OH (US); Huihe Zhu, Cincinnati, OH (US); Kevin James Finn, Blue Ash, OH (US)

(73) Assignee: Nitto Denko Avecia, Inc., Milford, MA (US)

( * ) Notice: Subject to any disclaimer, the term of this patent is extended or adjusted under 35 U.S.C. 154(b) by 152 days.

(21) Appl. No.: 12/989,268

(22) PCT Filed: Apr. 24, 2009

(86) PCT No.: PCT/EP2009/055012
§ 371 (c)(1), (2), (4) Date: Oct. 22, 2010

(87) PCT Pub. No.: WO2009/130328
PCT Pub. Date: Oct. 29, 2009

(65) Prior Publication Data
US 2011/0087014 A1   Apr. 14, 2011

Related U.S. Application Data

(60) Provisional application No. 61/047,524, filed on Apr. 24, 2008.

(51) Int. Cl.
C07H 21/00 (2006.01)
C12Q 1/68 (2006.01)

(52) U.S. Cl.
USPC .......................................... 536/25.3; 435/6.1

(58) Field of Classification Search
USPC .......................................... 536/25.3; 435/6.1
See application file for complete search history.

(56) References Cited

U.S. PATENT DOCUMENTS

| | | |
|---|---|---|
| 6,465,628 B1 | 10/2002 | Ravikumar et al. |
| 6,664,388 B2 | 12/2003 | Nelson |
| 6,858,715 B2 | 2/2005 | Ravikumar et al. |
| 6,887,990 B1 | 5/2005 | Bhan et al. |
| 7,199,236 B2 | 4/2007 | Ravikumar et al. |
| 7,339,052 B2 | 3/2008 | Reddy |
| 2004/0219577 A1 | 11/2004 | Ravikumar et al. |

FOREIGN PATENT DOCUMENTS
JP  1721907 A1  11/2006

OTHER PUBLICATIONS

Eritja, Ramon, et al—"A synthetic procedure for the preparation of oligonucleotides without using ammonia and its application for the synthesis of oligonucleotides containing 0-4-alkyl thymidines"; 1992, Tetrahedron vol. 48, Issue 20, pp. 4171-4182; 12 pgs.
Umemoto Tadashi, et al—"Nitromethane as a scavenger of acrylonitrile in the deprotection of synthetic oligonucleotides"; 2005, Tetrahedron Letters, Elsevier, vol. 46, No. 24: pp. 4251-4253; 3 pgs.

(Continued)

*Primary Examiner* — Jezia Riley
(74) *Attorney, Agent, or Firm* — Timothy E. Tinkler

(57) ABSTRACT

A process for manufacturing an oligonucleotide which comprises removing β-eliminating phosphorus-protecting groups, in particular β-cyanoethyl protective groups from a protected oligonucleotide, wherein said removing comprises contacting the protected oligonucleotide with an amine solution in a solvent which preferably does not consist of pyridine, wherein the conjugate acid of the amine has preferably a pKa of greater than 11.5, and wherein the concentration of the amine in the solution is less than 0.5 mole/liters.

16 Claims, 14 Drawing Sheets

(56) References Cited

OTHER PUBLICATIONS

Eritja, Ramon, et al—"Duplex-Stabilization Properties of Oligodeoxynucleotides Containing $N^2$-Substituted Guanine Derivatives"; 2000, Helvetica Chimica Acta, vol. 83, Issue 7, pp. 1417-1423, 7 pgs.

Jung, T., et al—"New latent amines for the coatings industry", 2003, Basel Switzerland, Ciba : Color & Lacquer; 5 pgs.

Foroughifar, Nasar, et al—"Basicity of substituted 2-pyridyl-1,1,3,3-tetramethylguanidines and aminopyridines in acetonitrile and water solvents", 1992, Can. J. Chem., vol. 70, pp. 2856-2858; 3 pgs.

Tosquellas, G., et al—"First synthesis of alternating SATE-phosphotriester/phosphodiester prooligonucleotides on solid support", 1998, Bioorganic Medicinal Chemistry Letters, Pergamon, vol. 20: pp. 2913-2918; 6 pgs.

Reese, Colin B., et al—"An approach to the desulfurization of oligonucleotide phosphorothioates"; Tetrahedron Letters, Pergamon, 2003, vol. 44, Issue 12, pp. 2501-2504; 4 pgs.

Kauppinen, Sakari, et al—"Locked nucleic acid (LNA): High affinity targeting of RNA for diagnostics and therapeutics"; 2005, Drug Discovery Today: Technologies, Elsevier, vol. 2, Issue 3, pp. 287-290; 4 pgs.

Wengel, Jesper—"Locked Nucleic Acid", 1998, Technology TM: A brief overview—EXIQON; Nucleic Acid Center, Univ. of Denmark; 7 pgs.

Nikiforov, Theo T., et al—"Straightforward Preparation and Use in Oligodeoxynucleotide Synthesis of 5'-O-(4,4'-dimethoxytrityl)-4-[S-(2-Cyanoethyl)]-Thiothymidine"; 1992, Tetrahedron Letters, Pergamon, vol. 33, Issue 17, pp. 2379-2382; 4 pgs.

Roelen, H. C. P. F., et al—"Solid-phase synthesis of oligodeoxynucleotides containing 4-alkoxythymidine residues"; 1992, Recueil des Travaux Chimiques des Pays-Bas; vol. 111/2, Issue 5, pp. 99-104; 7 pgs.

Szabo, Tomas, et al—"2-Cyanoethyl H-Phosphonate. A Reagent for the Mild Preparation of Nucleoside H-Phosphonate Monoesters"; 1995, Nucleosides and Nucleotides, 14, 3-5, pp. 715-716; 3 pgs.

Adams, Chris J., et al—"A convenient synthesis of S-cyanoethyl-protected 4-thiouridine and its incorporation into oligoribonucleotides"; 1994, Tetrahedron Letters, Pergamon, vol. 35, Issue 5, pp. 765-768; 4 pgs.

McGregor, A., et al—"Preparation of oligoribonucleotides containing 4-Thiouridine using Fpmp chemistry. Photo-crosslinking to RNA binding proteins using 350 nm irradiation", 1996, Nucleic Acids Research, vol. 24, Issue 16 pp. 3173-3180; 8 pgs.

Bologna, J.-C., et al—"The prooligonucleotide approach : synthesis of mixed sate-phosphotriester phosphodiester oligonucleotides"; 1999, Nucleosides & Nucleotides, vol. 18, No. 6-7, pp. 1433-1434; 3 pgs.

Merk, Claudia, et al—"Nucleotides, Part LXVII, The 2-Cyanoethyl and (2-Cyanoethoxy)carbonyl Group for Base Protection in Nucleoside and Nucleotide Chemistry", 2000, Helvetica Chimica Acta; vol. 83, Issue 12, 3198-3210; 13 pgs.

Beuck, C.—et al—"Convenient Synthesis of Oligodeoxynucleotides Containing 2'-Deoxy-6-thioinosine"; 2003, Nucleosides Nucleotides Nucleic Acids, vol. 22 ( 5-8) 635-639; 6 pgs.

Shimizu, M.—et al—"Solid-phase Synthesis of Oligodeoxyribonucleoside boranophosphates by the Boranophosphotriester Method"; 2006, J Organic Chemistry, vol. 71(11), 4262-4269; 8 pgs.

Figure 1 : IP-HPLC data
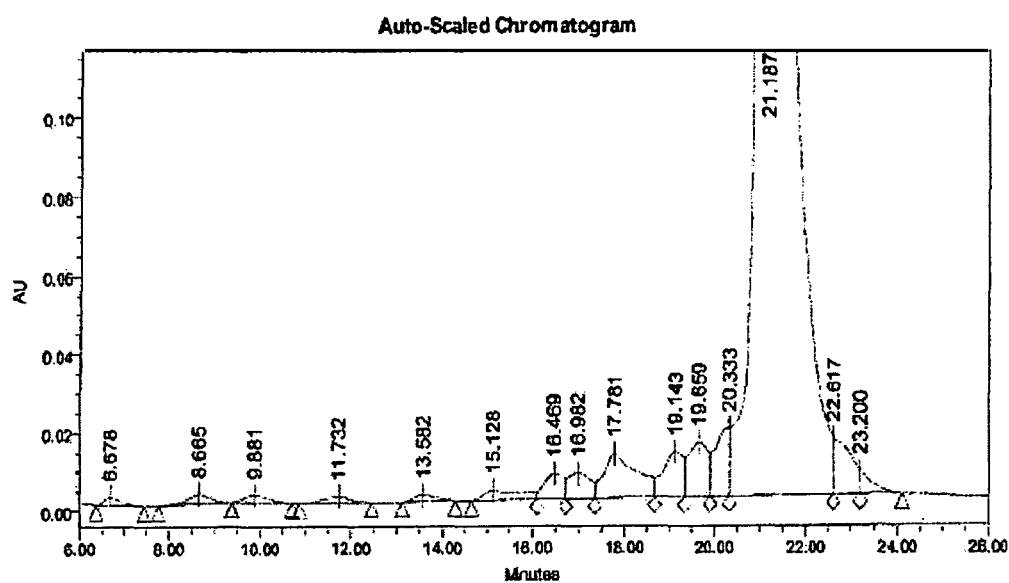

Figure 2 : LC/MS data
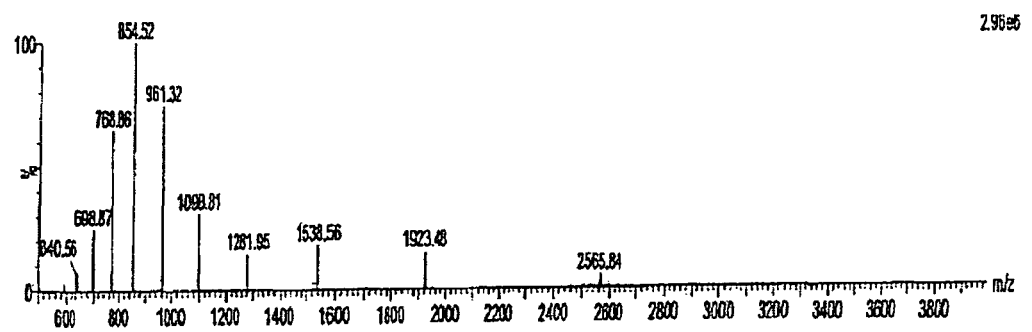
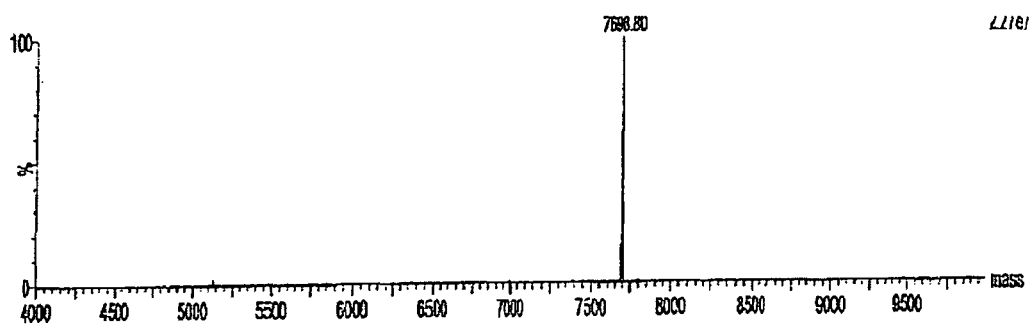

Figure 3 : RP-HPLC data
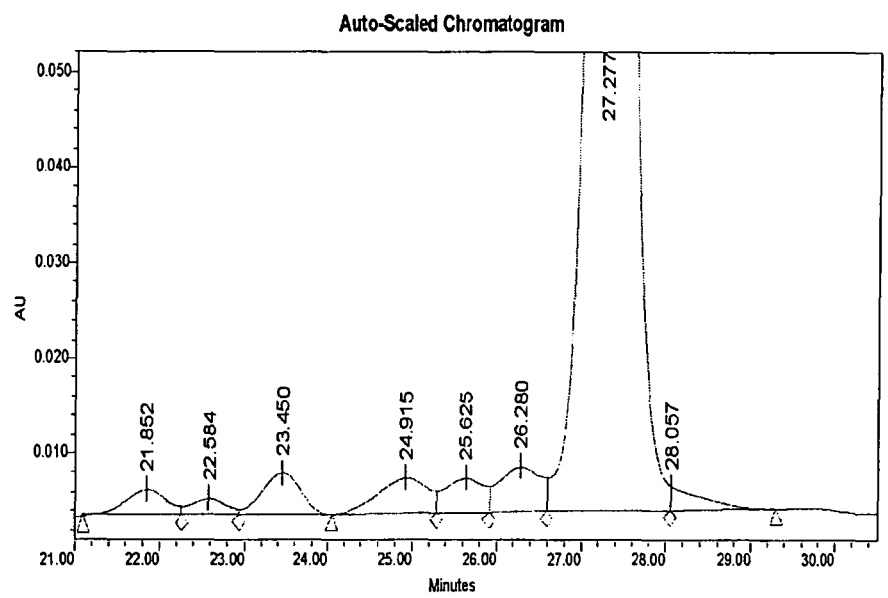

Figure 4 : LC/MS data
UV and Mass Trace(s)
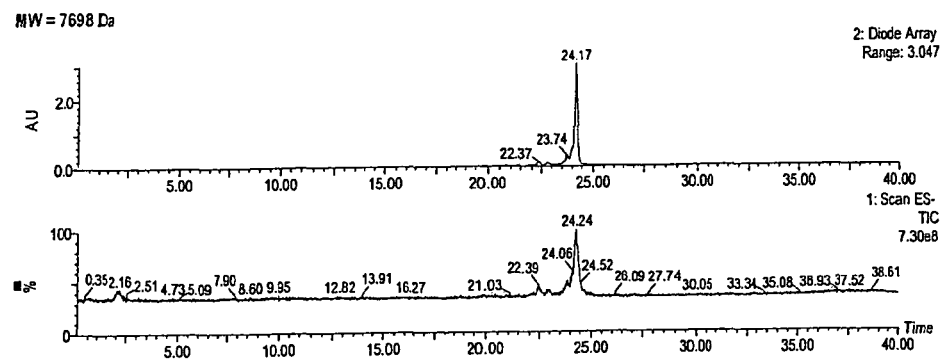
Mass Spectrum
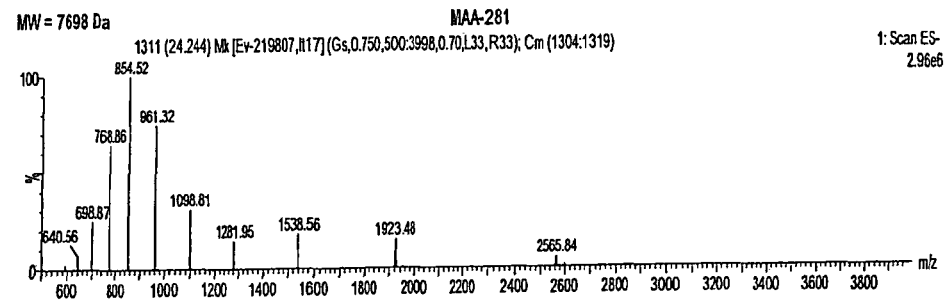
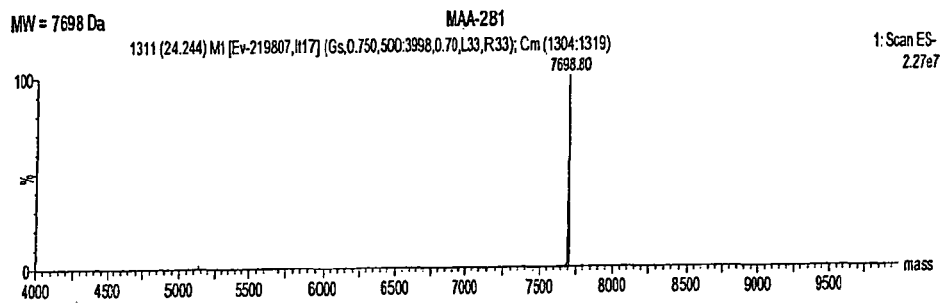

Figure 5 : RP-HPLC data
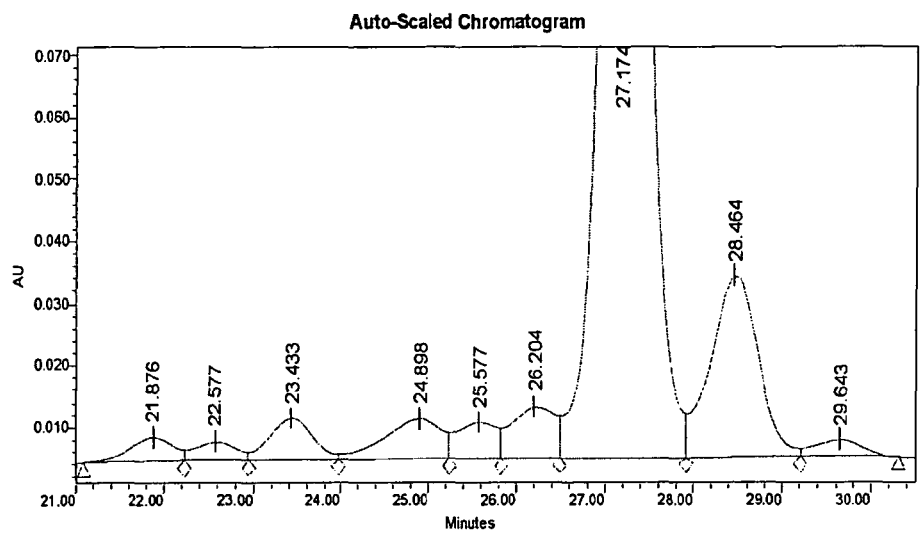
Peak Results
| | RT | Area | Height | % Area |
|---|---|---|---|---|
| 1 | 4.329 | 26632 | 1180 | 0.26 |
| 2 | 6.218 | 62140 | 2097 | 0.60 |
| 3 | 7.811 | 65939 | 1884 | 0.64 |
| 4 | 9.653 | 100862 | 2831 | 0.98 |
| 5 | 10.823 | 15644 | 509 | 0.15 |
| 6 | 12.615 | 145268 | 3272 | 1.41 |
| 7 | 14.440 | 68833 | 1825 | 0.67 |
| 8 | 16.659 | 98717 | 2029 | 0.96 |
| 9 | 18.623 | 71738 | 2002 | 0.69 |
| 10 | 20.346 | 73198 | 2184 | 0.71 |
| 11 | 21.876 | 141445 | 4009 | 1.37 |
| | RT | Area | Height | % Area |
|---|---|---|---|---|
| 12 | 22.577 | 104943 | 3169 | 1.02 |
| 13 | 23.433 | 237740 | 6886 | 2.30 |
| 14 | 24.898 | 310787 | 6674 | 3.01 |
| 15 | 25.577 | 187439 | 6010 | 1.81 |
| 16 | 26.204 | 285828 | 8438 | 2.77 |
| 17 | 27.174 | 7135325 | 222698 | 69.05 |
| 18 | 28.464 | 1096491 | 29373 | 10.61 |
| 19 | 29.643 | 104653 | 2794 | 1.01 |

Figure: 6A : LC/MS data
UV and Mass Trace(s)
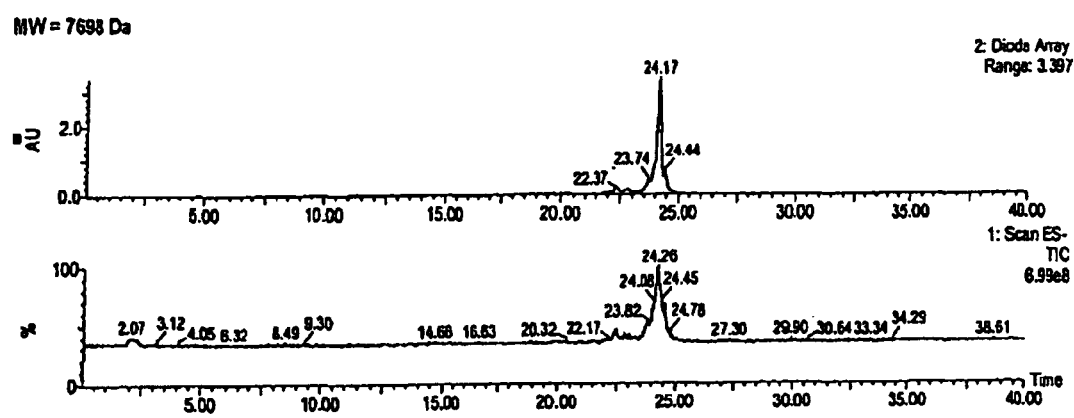
Mass Spectrum
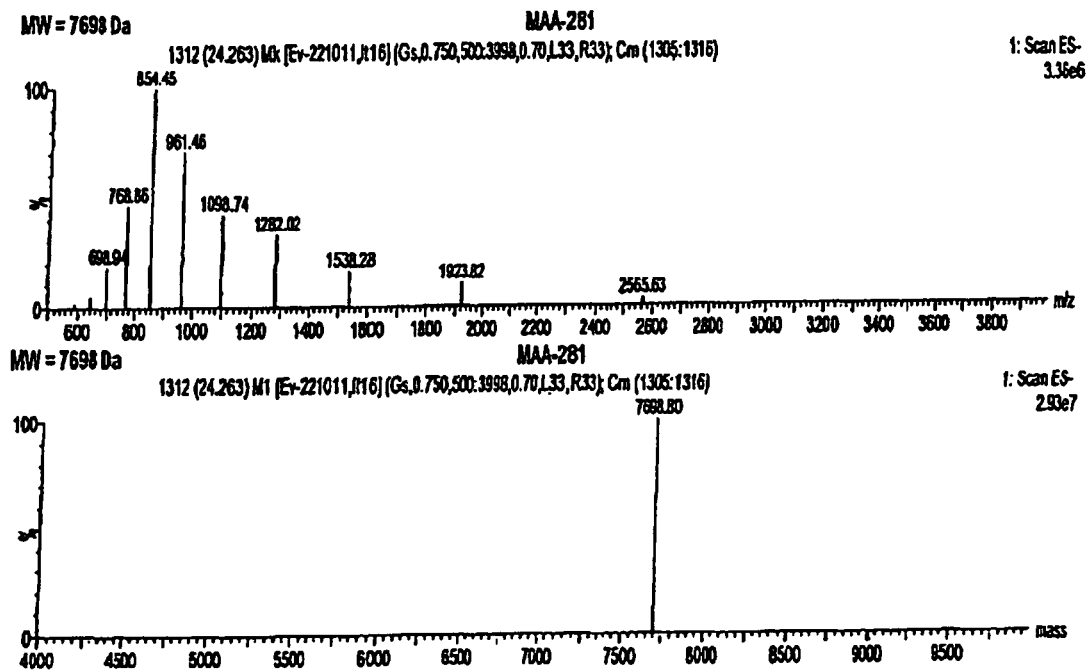

Figure: 6B : LC/MS data
UV and Mass Trace(s)
Mass Spectrum
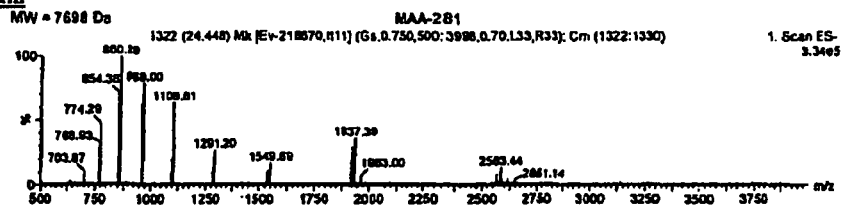
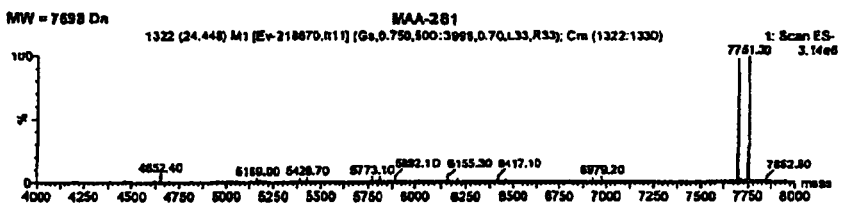
Figure 7 : RP-HPLC data
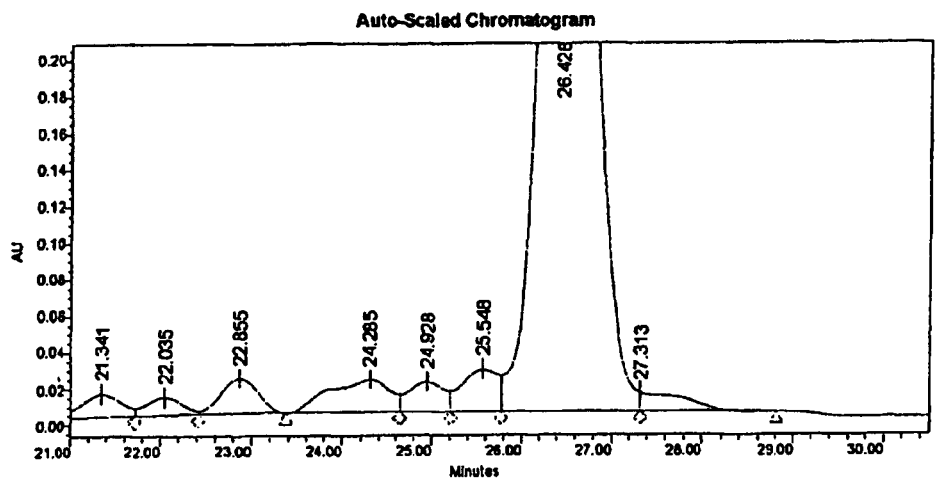
Peak Results
| | RT | Area | Height | % Area | | | RT | Area | Height | % Area |
|---|---|---|---|---|---|---|---|---|---|---|
| 1 | 7.063 | 54305 | 1357 | 0.19 | | 12 | 22.855 | 553165 | 19516 | 1.97 |
| 2 | 8.735 | 125147 | 3164 | 0.45 | | 13 | 24.265 | 864364 | 18043 | 3.08 |
| 3 | 9.777 | 88893 | 2599 | 0.32 | | 14 | 24.928 | 468283 | 16729 | 1.67 |
| 4 | 12.097 | 400078 | 7055 | 1.43 | | 15 | 25.548 | 662084 | 23458 | 2.36 |
| 5 | 13.985 | 200324 | 4821 | 0.71 | | 16 | 26.428 | 22687718 | 657858 | 80.95 |
| 6 | 16.280 | 335811 | 7272 | 1.20 | | 17 | 27.313 | 356724 | 10348 | 1.27 |
| 7 | 18.164 | 218058 | 5824 | 0.78 | | | | | | |

Figure 8 : RP-HPLC data
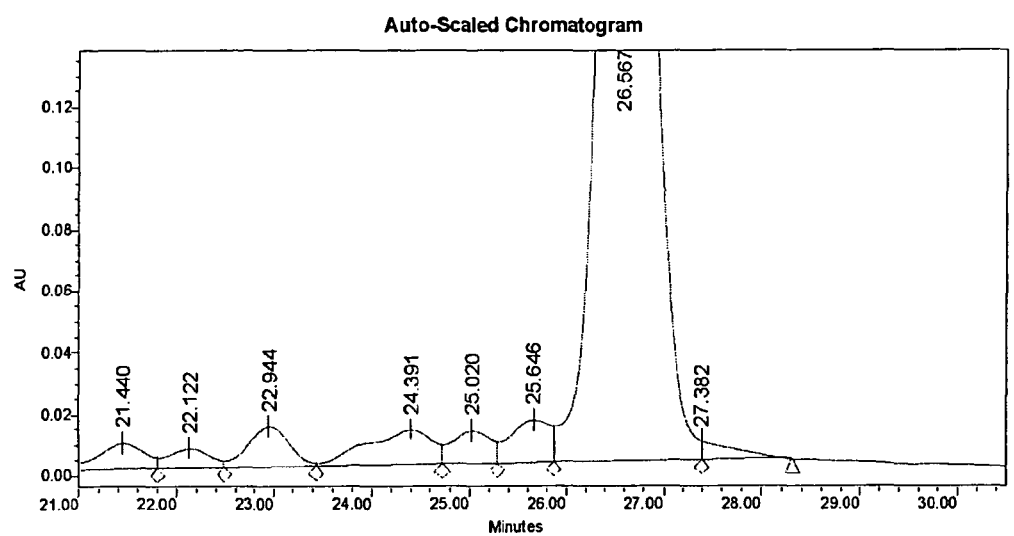

Figure 9 : LC/MS data
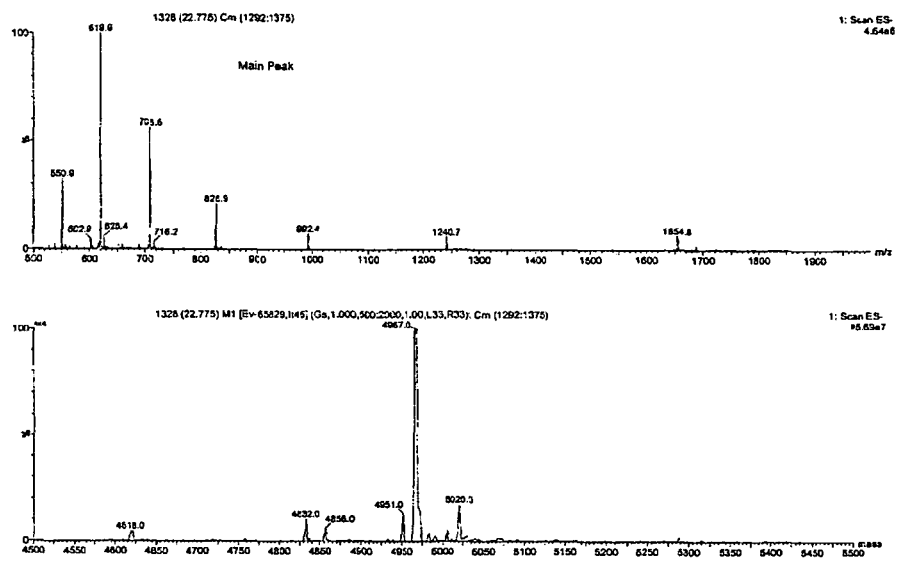

Figure 10 : LC/MS data
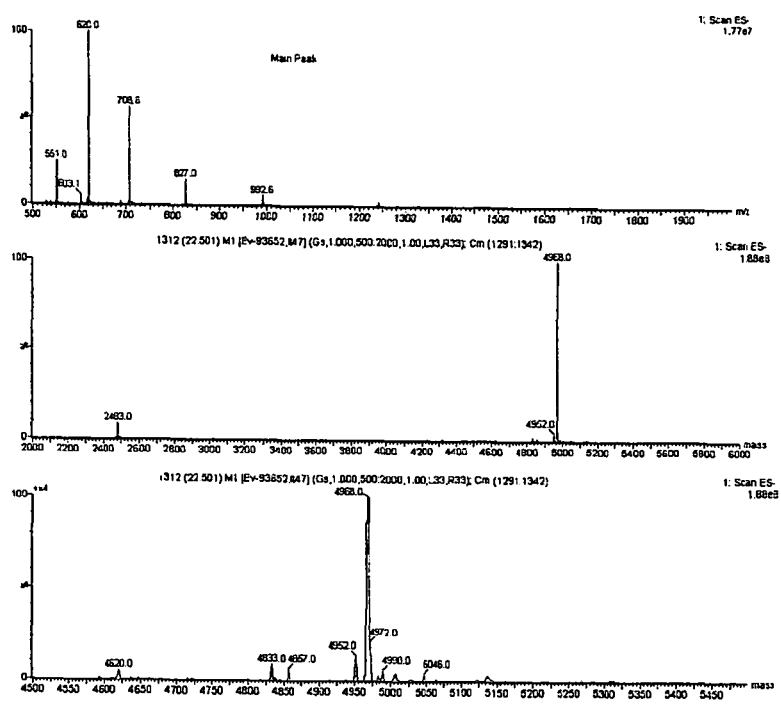

Figure 11 : RP-HPLC data
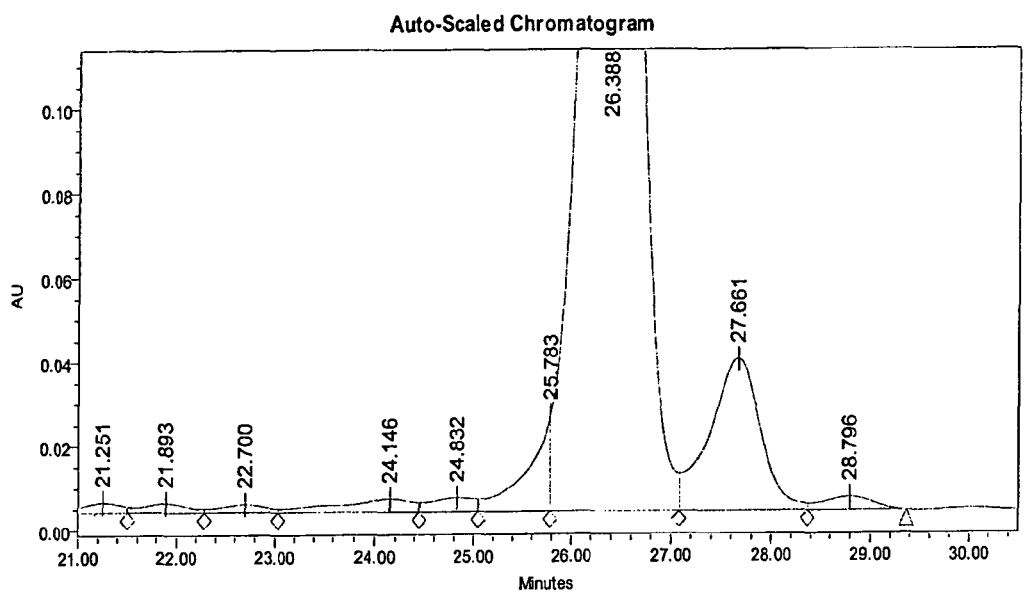
Peak Results
| | RT | Area | Height | % Area |
|---|---|---|---|---|
| 1 | 11.950 | 80541 | 1342 | 0.56 |
| 2 | 13.837 | 53838 | 1103 | 0.37 |
| 3 | 16.088 | 28086 | 976 | 0.19 |
| 4 | 18.117 | 50706 | 1720 | 0.35 |
| 5 | 19.814 | 25855 | 1060 | 0.18 |
| 6 | 21.251 | 68959 | 2347 | 0.48 |
| 7 | 21.893 | 71882 | 2199 | 0.50 |
| 8 | 22.700 | 59672 | 1839 | 0.41 |
| 9 | 24.146 | 162924 | 3075 | 1.13 |
| 10 | 24.832 | 103102 | 3307 | 0.71 |
| 11 | 25.783 | 364735 | 22753 | 2.52 |
| | RT | Area | Height | % Area |
|---|---|---|---|---|
| 12 | 26.388 | 12003542 | 357802 | 83.02 |
| 13 | 27.661 | 1273985 | 36218 | 8.81 |
| 14 | 28.796 | 111085 | 3198 | 0.77 |

Figure 12 : RP-HPLC data
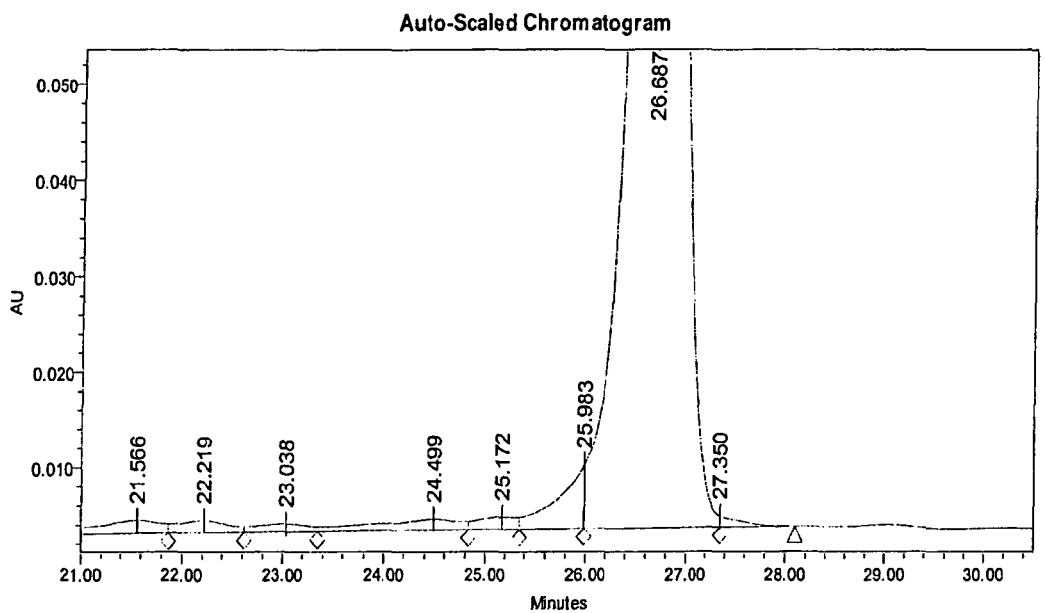
Peak Results
| | RT | Area | Height | % Area |
|---|---|---|---|---|
| 1 | 5.859 | 13102 | 758 | 0.23 |
| 2 | 7.576 | 19003 | 1040 | 0.33 |
| 3 | 8.892 | 109246 | 3966 | 1.89 |
| 4 | 10.421 | 28235 | 711 | 0.49 |
| 5 | 12.990 | 54848 | 1037 | 0.95 |
| 6 | 14.570 | 29234 | 777 | 0.51 |
| 7 | 16.597 | 25225 | 681 | 0.44 |
| 8 | 18.484 | 26216 | 766 | 0.45 |
| 9 | 20.155 | 17844 | 571 | 0.31 |
| 10 | 21.566 | 72486 | 1396 | 1.25 |
| 11 | 22.219 | 45963 | 1302 | 0.80 |
| | RT | Area | Height | % Area |
|---|---|---|---|---|
| 12 | 23.038 | 31816 | 852 | 0.55 |
| 13 | 24.499 | 72028 | 1164 | 1.25 |
| 14 | 25.172 | 36459 | 1311 | 0.63 |
| 15 | 25.983 | 117164 | 6664 | 2.03 |
| 16 | 26.687 | 5060433 | 166849 | 87.61 |
| 17 | 27.350 | 16690 | 1136 | 0.29 |

Figure 13 : RP-HPLC data
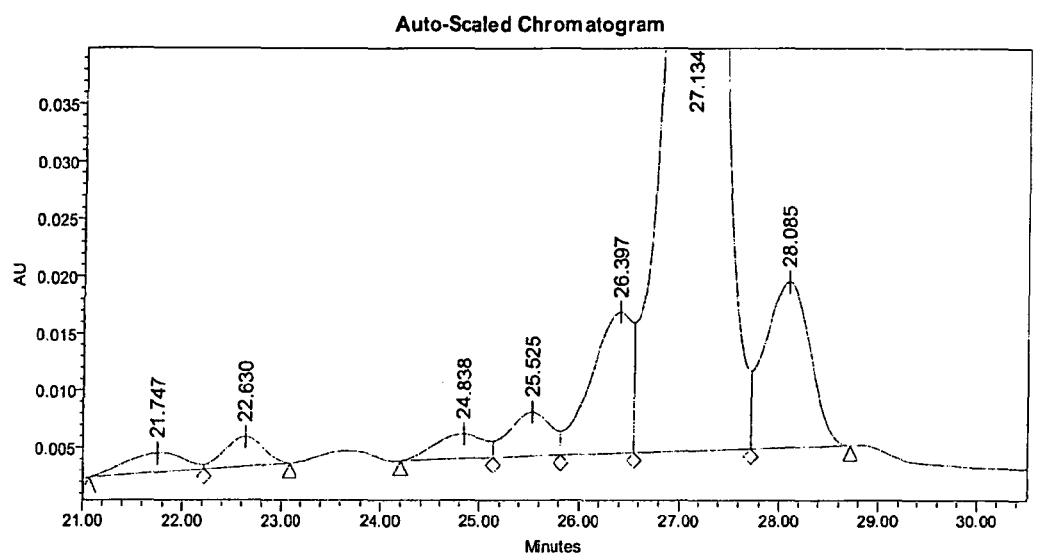

Figure 14 : RP-HPLC DATA
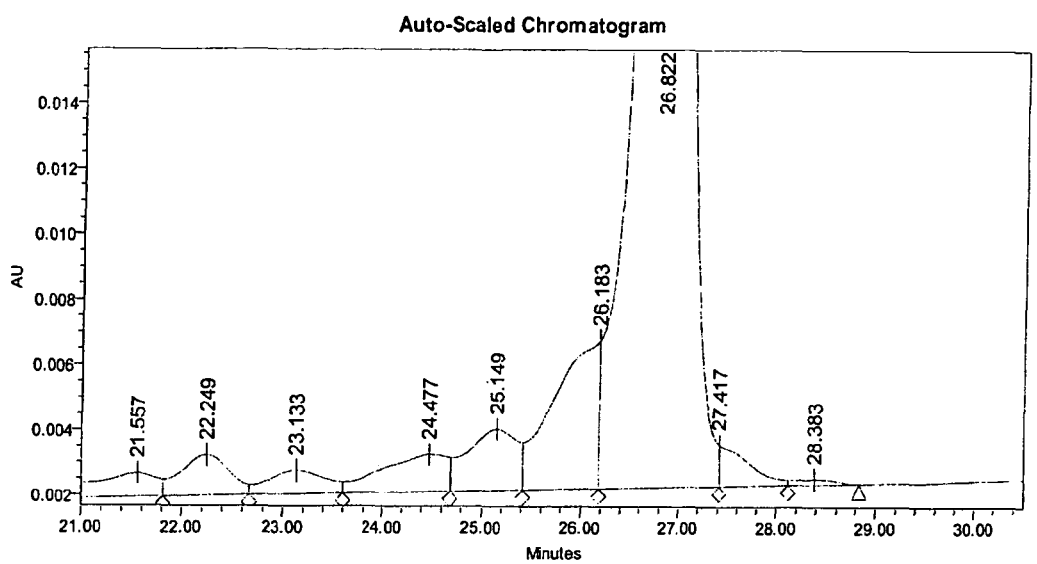
Peak Results
| | RT | Area | Height | % Area |
|---|---|---|---|---|
| 1 | 7.343 | 7058 | 159 | 0.35 |
| 2 | 9.337 | 11167 | 154 | 0.56 |
| 3 | 12.054 | 27983 | 431 | 1.40 |
| 4 | 14.108 | 24842 | 549 | 1.24 |
| 5 | 16.300 | 24771 | 501 | 1.24 |
| 6 | 18.298 | 20738 | 397 | 1.03 |
| 7 | 19.967 | 14205 | 290 | 0.71 |
| 8 | 21.557 | 35550 | 719 | 1.77 |
| 9 | 22.249 | 41463 | 1235 | 2.07 |
| 10 | 23.133 | 28720 | 716 | 1.43 |
| 11 | 24.477 | 51874 | 1137 | 2.59 |
| 12 | 25.149 | 66119 | 1885 | 3.30 |
| 13 | 26.183 | 142796 | 4543 | 7.12 |
| 14 | 26.822 | 1476667 | 47779 | 73.63 |
| 15 | 27.417 | 26562 | 1282 | 1.32 |
| 16 | 28.383 | 5011 | 172 | 0.25 |

PROCESS FOR THE MANUFACTURE OF OLIGONUCLEOTIDES

CROSS-REFERENCE TO RELATED APPLICATIONS

The present application is a U.S. national stage application under 35 U.S.C. §371 of International Application No. PCT/EP2009/055012 filed Apr. 24, 2009, which claims the benefit of U.S. application Ser. No. 61/047,524, filed Apr. 24, 2008, the whole content of which being herein incorporated by reference for all purposes.

The present invention relates to a process for the manufacture of oligonucleotides. Oligonucleotides and derivatives thereof are useful candidate drugs, for example, for cancer therapy.

The β-cyanoethyl protective group is commonly used as phosphorus protective group during synthesis of oligonucleotides in particular via the phosphoramidite approach. The deprotection of the cyanoethyl groups is one step in order to accede to the final product.

U.S. Pat. Nos. 6,858,715 and 7,199,236, the contents of which are incorporated by reference into the present specification, describe a process for deprotection of β-cyanoethyl protective groups wherein an amine, the conjugate acid of which has a pKa of from about 8 to about 11 must be used.

Eritja et al. Hely. Chim. Acta, Vol 83 (2000) p.1417-1423 disclose deprotection of β-cyanoethyl protected oligonucleotides with a 0.5 M concentrated DBU solution in acetonitrile.

It has now been found, surprisingly, that even a strong base the conjugate acid of which has a pKa of greater than 11.5, for example, of about 12, may be used under certain conditions to bring about substantially complete deprotection e.g. of β-cyanoethyl protective group while substantially avoiding formation of cyanoethyl adducts to nucleobases, in particular thymidine.

The invention concerns in consequence a process for manufacturing an oligonucleotide which comprises at least a step of removing β-eliminating phosphorus-protecting groups, in particular β-cyanoethyl protective groups from a protected oligonucleotide wherein said removing comprises contacting the protected oligonucleotide with an amine solution in a solvent which preferably does not consist of pyridine wherein the conjugate acid of the amine has preferably a pKa of greater than 11.5, and wherein the concentration of the amine in the solution is less than 0.5 mole/liters.

It has been found, surprisingly, that the process according to the invention allows for particularly efficient deprotection of phosphorus protected oligonucleotides, in particular of β-cyanoethyl protective groups, with high selectivity and yield. Undesirable side-reactions during deprotection can be substantially avoided.

BRIEF DESCRIPTION OF THE DRAWINGS

FIG. 1 shows IP-HPLC data from the analysis of the oligonucleotide product of Example 1.

FIG. 2 shows LC/MS data from the analysis of the oligonucleotide product of Example 1.

FIG. 3 shows RP-HPLC data from the analysis of the oligonucleotide product of Example 2.

FIG. 4 shows LC/MS data from the analysis of the oligonucleotide product of Example 2.

FIG. 5 shows RP-HPLC data from the analysis of the oligonucleotide product of comparative Example 3.

FIG. 6A shows LC/MS data from the analysis of the oligonucleotide product of comparative Example 3.

FIG. 6B shows a continuation of the LC/MS data from the analysis of the oligonucleotide product of comparative Example 3.

FIG. 7 shows RP-HPLC data from the analysis of the oligonucleotide product of Example 4.

FIG. 8 shows RP-HPLC data from the analysis of the oligonucleotide product of Example 5.

FIG. 9 shows LC/MS data from the analysis of the oligonucleotide product of comparative Example 6.

FIG. 10 shows LC/MS data from the analysis of the oligonucleotide product of Example 7.

FIG. 11 shows RP-HPLC data from the analysis of the oligonucleotide product of comparative Example 8.

FIG. 12 shows RP-HPLC data from the analysis of the oligonucleotide product of Example 9.

FIG. 13 shows RP-HPLC data from the analysis of the oligonucleotide product of comparative Example 10.

FIG. 14 shows RP-HPLC data from the analysis of the oligonucleotide product of Example 11.

The concentration of the amine in the solution is higher than 0 mole/liter. It is preferably equal to or higher than 0.03 moles/liter. The concentration of the amine in the solution is often lower than or equal to 0.4, preferably lower than or equal to 0.3 moles/liter, more preferably, lower than or equal to 0.25 moles/liter. Such preferred concentration can be, for example lower than or equal to 0.15 moles/liter or lower than or equal to 0.1 moles/liter. An amine concentration of about 0.05 moles/liter gives good results.

The total amount of the amine which is contacted with the protected oligonucleotide can vary. In one embodiment this amount is such that the molar ratio between the amine and the protective groups, in particular β-cyanoethyl protective groups which are to be removed is equal to or greater than 1.

In another embodiment this amount is such that the total amount of amine which is contacted with the protected oligonucleotide is such that the molar ratio between the amine and the protective groups, in particular β-cyanoethyl protective groups, which are to be removed is equal to or greater than 0.01 and equal to or lower than 0.9, preferably about 0.1.

The term "oligonucleotide", in the frame of the present invention, denotes in particular an oligomer of nucleoside monomeric units comprising sugar units connected to nucleobases, said nucleoside monomeric units being connected by internucleotide bonds. An "internucleotide bond" refers in particular to a chemical linkage between two nucleoside moieties, such as the phosphodiester linkage typically present in nucleic acids found in nature, or other linkages typically present in synthetic nucleic acids and nucleic acid analogues. Such internucleotide bond may for example include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group. Typical internucleotide bonds are diesters of phosphoric acid or its derivatives, for example phosphates, thiophosphates, dithiophosphate, phosphoramidates, thio phosphoramidates.

The term "nucleoside" is understood to denote in particular a compound consisting of a nucleobase connected to a sugar. Sugars include, but are not limited to, furanose ring such as ribose, 2'-deoxyribose and non-furanose ring such as cyclohexenyl, anhydrohexitol, morpholino. The modifications, substitutions and positions indicated hereinafter of the sugar included in the nucleoside are discussed with reference to a furanose ring, but the same modifications and positions also apply to analogous positions of other sugar rings. The sugar may be additionally modified. As non limitative examples of the modifications of the sugar mention can be notably made of modifications at e.g. the 2'-or 3'-position, in particular 2'-position of a furanosyl sugar ring including for instance hydrogen; hydroxy; alkoxy such as methoxy, ethoxy, allyloxy, isopropoxy, butoxy, isobutoxy, methoxyethyl, alkoxy, phenoxy; azido; amino; alkylamino; fluoro; chloro and bromo; 2'-4'- and 3'-4'-linked furanosyl sugar ring modifications, modifications in the furanosyl sugar ring including for instance substitutions for ring 4'-O by S, $CH_2$, NR, CHF or $CF_2$.

The term "nucleobase" is understood to denote in particular a nitrogen-containing heterocyclic moiety capable of pairing with a, in particular complementary, nucleobase or nucleobase analog. Typical nucleobases are the naturally occurring nucleobases including the purine bases adenine (A) and guanine (G), and the pyrimidine bases thymine (T), cytosine (C) and uracil (U), and modified nucleobases including other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, and fluorinated bases. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Other potentially suitable bases include universal bases, hydrophobic bases, promiscuous bases and size-expanded bases.

In the process according to the invention, the solvent often comprises a halogenated compound, such as a chloroalkane comprising 1 or 2 carbon atoms such as methylene chloride or 1,2-dichloroethane. Methylene chloride is preferred as chlorosolvent.

A solvent comprising a cyanoalkyl compound is preferred. Acetonitrile is preferred as cyanoalkyl compound.

A solvent consisting essentially of aforesaid compounds is preferred. More particularly, the solvent consists preferably of acetonitrile.

Internucleotide bond protected by certain β-eliminating phosphorus-protecting groups ($R_t$) used in the present invention may be represented in the following formula I

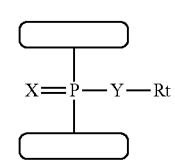

wherein each X and Y are independently O, S or NR;
wherein Rt is -C($R_1$)$_2$—C($R_1$)$_2$—W or C($R_1$)$_2$—(CH—CH)$_p$—C(R1)$_2$—W,
and wherein each $R_1$ is independently H or lower alkyl; W is an electron withdrawing group; p is 0 to 3.

In particularly preferred embodiments, the β-eliminating phosphorus-protecting groups ($R_t$) is -$CH_2$—$CH_2$—C≡N or —$CH_2$—(CH—CH)$_p$—C≡N, where p is an integer from 1 to 3, with —$CH_2$—$CH_2$—C≡N or —$CH_2$—CH=CH—$CH_2$—C≡N being preferred, and with -$CH_2$—$CH_2$—C≡N being particularly preferred.

In certain embodiments of the process according to the invention, the protected oligonucleotide is contacted with the amine for a reaction time of at least 200 minutes. The reaction time is preferably from 240 to 600 minutes, and more preferably from 300 to 400 minutes. A reaction time of about 360 minutes has given good results.

Reaction time is typically understood to denote the period of time during which the protected oligonucleotide is contacted with the amine solution.

In another, preferred embodiment, the reaction time is less than 200 min., typically less than or equal to 100 minutes, more preferably less than or equal to 30 minutes. A reaction time equal to or less than 20 minutes is more particularly preferred, a reaction time equal to or less than 15 minutes is most particularly preferred. In this preferred embodiment, the reaction time is typically more than or equal to 3 minutes, more preferably more than or equal to 6 minutes.

It has been found, surprisingly, that it is possible to achieve very efficient deprotection also with low reaction times.

In the different embodiments of the process according to the invention, the removal is generally carried out at a temperature of from 0 to 80° C. preferably from 10 to 60° C. A temperature of about 20 to 30° C. has given good results.

In the process according to the invention, the protected oligonucleotide can be obtained for example by solution-phase or, preferably, solid phase coupling of protected nucleotides. Coupling techniques providing protected oligonucleotides as described above are known per se.

In the different embodiments of the process according to the invention, the protected oligonucleotide is preferably attached to a solid support. "Solid support" denotes in particular any particle, bead, or surface upon which synthesis of an oligonucleotide occurs. Solid supports which can be used in the different embodiments of the process according to the invention are selected for example from inorganic supports and organic supports. Inorganic supports are preferably selected from silica gel and controlled pore glass (CPG). Organic supports are preferably selected from highly crosslinked polystyrene, Tentagel (grafted copolymers consisting of a low crosslinked polystyrene matrix on which polyethylene glycol (PEG or POE) is grafted), polyvinylacetate (PVA), Poros—a copolymer of polystyrene/divinyl benzene, aminopolyethyleneglycol and cellulose. The solid support is more preferably selected from highly crosslinked polystyrene. The protected oligonucleotide can be attached to the solid support by means of a linkage. Linkages are known in the art as chemical moieties comprising a covalent bond or a chain of atoms that covalently attach a solid support to a nucleoside, nucleotide or oligonucleotide. Commercially available are so called "standard solid supports" carrying a nucleoside that has been pre-attached via a linker. This nucleoside will become the 3'- or 5'-terminal residue of the final oligonucleotide after the cleavage and deprotection step. Suitable linkers which can be used in this embodiment of the invention are for example succinyl, carbonate, carbamate. The succinyl linker is most preferred. The standard solid supports do carry the 3'- or 5'-terminal nucleoside.

Solid supports without the 3'- or 5'-nucleoside pre-attached, namely the "universal" solid supports are also known in the art and commercially available. Those supports do not have the intended 3'- or 5'-terminal nucleoside attached. Rather, the corresponding terminal nucleoside or residue is added in the first cycle, generating an undesired phosphate or thiophosphate linkage between this nucleoside and the universal support. This approach requires that the undesired phosphate or thiophosphate linkage to be removed during the cleavage and/or deprotection step. Typical examples of the "universal" solid support are shown in scheme 1.

Scheme 1

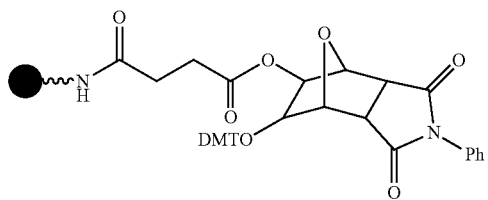

Universal Support Type 1

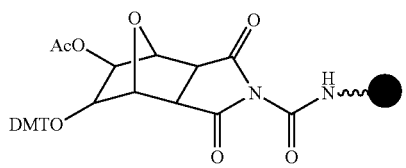

Universal Support Type 2

It has been found, surprisingly, that the process according to the invention allows for selectively deprotecting phosphorus protecting groups without cleaving the oligonucleotide from the support.

In a particular aspect of this embodiment, the solid support containing the protected oligonucleotide may be contained in a device such as a column having inlet and outlet openings. According to this embodiment, the amine may be contacted with the protected oligonucleotide by passing the amine solution through the said device. Preferably, the process is automated using a commercially available automated synthesizer, programmed to deliver the amine in a solvent through one of the delivery lines of the synthesizer.

Advantageously, the amine solution may be passed through the column in an amount of at least 1 often at least 2 column volumes, most preferably in an amount of at least 5 column volumes. Advantageously, the amine solution may be passed through a column in an amount of at most 100 column volumes, preferably in an amount of at most 60 column volumes.

In a particular embodiment, the process according to the invention comprises the following steps
(a) a protected oligonucleotide attached to a solid support is synthesized by solid-phase coupling technique;
(b) the protected olignucleotide is subjected to deprotection of the phosphorus protecting groups as described herein;
(c) the oligonucleotide attached to the support is optionally treated to reduce its amine content;
(d) the oligonucleotide is cleaved from the support.

Step (c) can be for example a washing operation, for example with the solvents described herein, in particular acetonitrile. Step (d) is suitably selected from a treatment with a protic base solution or a nucleophilic base solution. Examples of suitable bases are selected from aqueous ammonia, methylamine and ammonia/methylamine mixtures.

In the different embodiments of process according to the invention, an amine is generally used the conjugate acid whereof has a pKa which is greater than 11.5 and is up to 12.5. Preferably, an amine is used the conjugate acid whereof has a pKa of about 12. The term pKa is usually defined as the negative base 10 logarithm of the equilibrium dissociation constant of the conjugated acid in an aqueous solution in particular measured at 25° C. Non limitive examples of such suitable amines are DBU (1,8-diazabicyclo[5.4.0]undec-7-ene), DBN (1,5-Diazabicyclo[4.3.0]non-5-ene), TMG (tetramethylguanidine), TBD (triazabicyclodecene) An example of such suitable amine is DBU
(Diazabicycloundecene). DBU is most preferred.

In a most preferred embodiment, the invention concerns a process for manufacturing an oligonucleotide which comprises at least a step of removing β-cyanoethyl protective groups from a protected oligonucleotide wherein said removing comprises contacting the protected oligonucleotide with DBU, preferably in a concentration as described above in a solvent comprising acetonitrile. In this embodiment, the reaction time is preferably as described above.

The different embodiments of the process according to the invention can be applied, for example, to the synthesis of oligonucleotides selected from DNA, RNA, BNA, UNA and derivatives thereof. LNA, ENA are typical examples of BNA. Examples of certain oligonucleotides can be defined as in the formula in col .2 1.1- col. 3 1.15 of U.S. Pat. No. 6,456,628.

DNA denotes in particular a polymer of deoxyribonucleic acid units, RNA denotes in particular a polymer of ribonucleic acid units, BNA's denotes in particular a polymer of bicyclic nucleic acids, LNA denotes in particular a polymer of locked nucleic acid units, ENA denotes in particular a polymer of 2'-0,4'-C-ethylene bridged nucleic acid and UNA's denotes in particular a polymer of unlocked nucleic acids.

As other non limitative examples of naturally occurring nucleobases useful in the present invention, can be mentioned adenine, guanine, cytosine, uracil, and thymine. As non limitative examples of non-naturally occurring and rare naturally occurring nucleobases can be mentioned xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine.

Suitable nucleobase protecting groups are known to persons skilled in the art such as benzoyl, isobutyryl, acetyl, phenoxyacetyl, aryloxyacetyl, phthaloyl, 2-(4-nitro-phenyl) ethyl, pent-4-enoyl, dimethylformamidine (dmf), dialkylformamidine, and dialkylacetamidine.

Suitable 5'-hydroxyl protection groups include, but are not limited to trityl groups, preferably a dimethoxytrityl group (DMTr) or a monomethoxytrityl group (MMTr). Other suitable 5'-protection groups include, but are not limited to tert-butyl dimethylsilyl (TBDMS), levulinyl, benzoyl, fluorenemethoxycarbonyl (FMOC), 9-phenylthioxanthen-9-yl (S-pixyl).

Suitable 2'-protecting groups used in RNA synthesis include, but are not limited to 2'-O-protecting groups: tert-butyl dimethylsilyl (TBDMS), 9-phenylxanthen-9-yl (Px), 9-phenylthioxanthen-9-yl(SPx),1- [(2-chloro-4methyl) pheny]-4-methoxypiperidin-4-yl (Ctmp), 1- (2-fluorophenyl)-4-methoxypiperidin-4-yl (Fpmp), [2-(methylthio)phenyl]thiomethyl (MTPM), methoxypiperidin-4-yl (Fpmp), [2-(methylthio)phenyl]thiomethyl (MTPM), bis-(Acetoxyethyloxy)methylester (ACE), (1-methyl-1-methoxyethyl)(MME),methoxy(ethoxymethyl(MEM), p-nitrophenylethylsylfonyl (NPES), p-cyanophenylethylsylfonyl (CPES), carbomethoxyethylsulfonyl (CEMS), Triisopropylsilylxyxyethyl (TOM) and 2' silyl-containing thiocarbonate protecting group.

In the different embodiments of the process according to the invention, the protected oligonucleotide generally contains β-cyanoethyl protected phosphate and/or β-cyanoethyl protected phosphorthioate and/or β-cyanoethyl protected phosphordithioate and/or β-cyanoethyl protected phosphoramidate and/or β-cyanoethyl protected thiophosphoramidate bonds In the preferred different embodiments of the process according to the invention, the protected oligonucleotide generally contains β-cyanoethyl protected phosphate and/or β-cyanoethyl protected phosphorthioate bonds.

In the following, some especially preferred specific embodiments of the process of the present invention are given.

One specific embodiment of the invention concerns a process for manufacturing an oligonucleotide which comprises at least a step of removing β-cyanoethyl protective groups from a protected oligonucleotide wherein said removing comprises contacting the protected oligonucleotide with DBU in a concentration as described above, wherein the oligonucleotide is attached to a solid support and the solvent is preferably acetonitrile.

In another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is DNA and is attached to a solid support. The amine preferably is DBU. The solvent preferably is acetonitrile. In another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above wherein the oligonucleotide is RNA and is attached to a solid support. The amine preferably is DBU. The RNA is preferably 2'-O-TBDMS or 2'-O-alkyl RNA. The solvent preferably is acetonitrile.

In still another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is LNA and is attached to a solid support. The amine preferably is DBU. The LNA preferably comprises 2'-O,4'-C-methylene-β-D-ribofuranosyl nucleotides. The solvent preferably is acetonitrile.

In still another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is BNA and is attached to a solid support. The amine preferably is DBU. The BNA preferably comprises 2'-O,4'-C-bridged nucleotides. The solvent preferably is acetonitrile.

In still another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is ENA and is attached to a solid support. The amine preferably is DBU. The ENA preferably comprises 2'-O,4'-C-ethylene-bridged nucleotides. The solvent preferably is acetonitrile.

In still another specific embodiment, the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is UNA and is attached to a solid support. The amine preferably is DBU. The UNA preferably comprises 2',3'-seco RNA nucleotides. The solvent preferably is acetonitrile.

Yet another specific embodiment of the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is attached to a solid support, wherein the supported oligonucleotide is present in a column, and the solution of the base is passed through the column. The amine preferably is DBU. In this embodiment, the solvent preferably is acetonitrile. Preferably, the process is performed while continuously circulating the amine solution through the column.

A further specific embodiment of the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above, wherein the oligonucleotide is attached to a solid support, as described above, in particular a polystyrene support. The preferred amine is DBU, the preferred solvent is acetonitrile.

Another specific embodiment of the invention concerns a process for manufacturing an oligonucleotide which comprises at least a step of removing β-cyanoethyl protective groups from a protected oligonucleotide wherein said removing comprises contacting the protected oligonucleotide with an amine the conjugate acid of which has a pKa of greater than 11.5 in a concentration as described above wherein the oligonucleotide is attached to a solid support, the oligonucleotide comprises β-cyanoethyl protected groups selected from the group consisting of β-cyanoethyl protected phosphate, β-cyanoethyl protected phosphorthioate, β-cyanoethyl protected phosphordithioate, β-cyanoethyl protected phosphoramidate, β-cyanoethyl protected thiophosphoramidate or 2 or more thereof. The amine preferably is DBU. The solvent preferably is acetonitrile.

Advantages of the process of the present invention include effective removal of protective groups, in particular β-cyanoethyl groups. It allows the treatment of oligonucleotides attached to a solid support without causing cleavage of them from the support.

While the foregoing description and following examples are essentially drawn to use of amine bases wherein the conjugate acid of the amine has a pKa of greater than 11.5, it is believed that the removal of protective groups, in particular β-cyanoethyl groups from protected oligonucleotides may be advantageously carried out by using solutions of other organic bases soluble in organic solvents in the concentration and according to the process conditions described herein before. Examples of such other bases include an amine the conjugate acid whereof has a pKa of from 8 to 11.5, such as for example alkyl amines, in particular diethylamine, triethylamine or piperidine.

The examples here after are intended to illustrate the invention without however limiting it.

EXAMPLES

In these examples and throughout this specification the abbreviations employed are defined as follows:

CNET adduct means $N^3$-cyanoethyl modified thymidine resulting from the reaction with acrylonitrile generated during removal of the 2-cyanoethyl protecting group from the P-centers of the synthesized oligonucleotide, FL35 means Fineline 35 column, CT means contact time, CV means column volumes.

Example 1

Synthesis of fully modified
5'-d(TCGTCGTTTTGTCGTTTTGTCGTT)-3'

Phosphorothioate 24-mer

The synthesis of the above sequence (SEQ ID NO:1) was performed on a AKTA 100 synthesizer using a FL35 column at 3 mmol synthesis scale, using the cyanoethyl phosphoramidites obtained from ChemGenes (and ThermoFisher) and GE Primer support loaded at 200 umoles per gram. At the end of synthesis the terminal 5'-O-protecting group 4,4-dimethoxytrityl (DMTr) was removed while oligonucleotide product was still attached to the solid support, prior to the amine wash. Amine wash was performed using 0.05M solution of DBU (1,8-Diazabicyclo[5.4.0]undec-7-en) in acetonitrile for at least 200 min, using 10-60 column volumes (CV) of the decyanoethylating reagent. Subsequently, de-cyanoethylated oligonucleotide product was removed from the synthesis column and treated with concentrated aqueous ammonia (~30% solution in water) at 55° C. for 16-24 hrs and analyzed by analytical ion exchange HPLC and LC/MS (FIGS. 1 and 2). Examples 2, 3, 4 and 5: Synthesis of modified 24 mer wherein all internucleotide bonds are phosphorothioate linkages 5'-d(TCGTCGTMGTCGTTTTGTCGTT)-3' (SEQ ID NO:1)

General procedure

The synthesis of the phosphorothioate of SEQ ID NO:1 was performed on an ÅKTA 100 synthesizer using a FL35 column at 3 mmol synthesis scale using commercially available phosphoramidites and GE Primer support having a loading of 206 µmol/g. At the end of the synthesis on solid support, the terminal 5'-O-4,4-dimethoxytrityl (DMTr) protecting group was removed on column by treatment with dichloroacetic acid. The solid support was then dried and repacked portionwise into 1.2 ml fixed columns (0.05 mmol scale) or 6.3 ml fixed columns (0.25 mmol scale) for a study of decyanoethylations using various concentrations of DBU (1,8-Diazabicyclo[5.4.0]undec-7-en) solution at various contact times, using various column volumes (CV) of the decyanoethylating reagent. In the comparative example, no contacting with DBU was carried out. Data are summarized in Table 1. For all examples, the decyanoethylated oligonucleotide product was treated with concentrated aqueous ammonia (~30% wt solution in water) at 55° C. for 16 hrs and analyzed by analytical RP-HPLC and LC/MS.

TABLE 1

| Example | Scale (mmol) | DBU in ACN [M] | CT [min] (a) | Amount in CV (b) | HPLC results | LC-MS results |
|---|---|---|---|---|---|---|
| 2 | 0.05 | 0.05M | 360 | 60 | FIG. 3 | FIG. 4 |
| 3 (Comparative) | 0.05 | — | — | — | FIG. 5 | FIG. 6 |
| 4 | 0.25 | 0.2M | 15 | 5 | FIG. 7 | — |
| 5 | 0.25 | 0.05M | 360 | 30 | FIG. 8 | — |

(a) CT = contact time;
(b) CV = column volumes

HPLC and LC-MS data are shown in FIGS. 3 and 4. SEQ ID NO:1 is eluting at 27.174 min, the CNET adduct is eluting at 28.464 min. SEQ ID NO:1 has a theoretical MW 7698 Da; the CNET adduct has theoretical MW of 7751 Da.

Examples 6 and 7: Synthesis of modified 15-mer, wherein all internucleotide bonds are phosphorothioate linkages 5'-CcA ttG Tca CaC tCC-3' (upper case LNA, lower case DNA) (SEQ ID NO:2)

The synthesis of the phosphorothioate of the SEQ ID NO:2 was carried out using a FL35 column at 3.6 mmol scale on an Åkta 100 synthesizer and using GE Primer support and commercially available phosphoramidite monomers. At the end of the synthesis, the terminal 5'-O- 4,4-dimethoxytrityl (DMTr) protecting group was removed while the oligonucleotide product was still attached to the solid support. The solid support was then dried and repacked portionwise into 1.2 ml fixed columns (0.05 mmol scale) or 6.3 ml fixed columns (0.25 mmol scale) for a study of decyanoethylation using various concentrations of DBU (1,8-Diazabicyclo[5.4.0]undec-7-en) solutions at various contact times, using various column volumes (CV) of the decyanoethylating reagent. In the comparative example, no contacting with DBU was carried out. Data are summarized in Table 2. For all examples, the de-cyanoethylated oligonucleotide product was treated with concentrated aqueous ammonia (~30% solution in water) at 55° C. for 16 hrs and analyzed by analytical RP-HPLC and LC/MS. In LC-MS data are shown in FIG. 9. SEQ ID NO:2 and the CNET adduct are eluting at the same time. Identification and quantification of both compounds was performed by LC/MS. SEQ ID NO:2 has a theoretical MW of 4967 Da; the CNET adduct has theoretical MW of 5020 Da.

The decyanoethylation treatments were also extended to the 1 mmol scale with favorable results (data not shown).

Examples 8, 9, 10 and 11: Synthesis of modified 24 mer wherein all internucleotide bonds are phosphorothioate linkages 5'-d(TCGTCGTTTTGTCGTTTTGTCGTT)-3' (SEQ ID NO:1)

The synthesis of the phosphorothioate of SEQ ID NO:1 was carried out on two different universal supports (Universal Support Type 1 and 2 (Scheme 1)) using a 6.3 mL fixed column and an Åkta 100 synthesizer and commercially available phosphoramidite monomers at scale of 0.215 and 0.156 mmol, respectively. The use of universal supports necessitates an additional coupling for the incorporation of the first nucleoside at the 3' end. At the end of the synthesis, the terminal 5'-O- 4,4-dimethoxytrityl (DMTr) protecting group was removed while the oligonucleotide product was still attached to the solid support. The support was dried under vacuum and part of the support was repacked into 1.2 mL fixed columns (0.043 & 0.025 mmol scale, respectively) for a study of decyanoethylation using various concentrations of DBU (1,8-Diazabicyclo[5.4.0]undec-7-en) solutions at various contact times, using various column volumes (CV) of the decyanoethylating reagent. In the comparative example, no contacting with DBU was carried out. Data are summarized in Table 3. For all examples, the de-cyanoethylated oligonucleotide product was treated with concentrated aqueous ammonia (~30% solution in water) according to the condition suggested by the manufacture of the supports and analyzed by analytical RP-HPLC.

TABLE 3

| Example | Scale (mmol) | Universal support type | DBU in ACN [M] | CT [min] (a) | Amount in CV (b) | HPLC results |
|---|---|---|---|---|---|---|
| 8 (Comparative) | 0.043 | 1 | — | — | — | FIG. 11 |
| 9 | 0.043 | 1 | 0.2M | 30 | 10 | FIG. 12 |
| 10 (Comparative) | 0.025 | 2 | — | 0 | — | FIG. 13 |
| 11 | 0.025 | 2 | 0.2M | 30 | 10 | FIG. 14 |

(a) CT = contact time;
(b) CV = column volumes

SEQ ID NO: 1 is eluting at 26.388 min, the CNET adduct is eluting at 27.661 min, as shown in FIG. 11.

The examples show that the process according to the invention allows for efficient and selective deprotection of phosphorus-protecting groups even with very low concentration of base. In particular, formation of undesired CNET adducts can be substantially avoided.

TABLE 2

| Example | Scale (mmol) | DBU in ACN [M] | CT [min] (a) | Amount in CV (b) | data | LC-MS results SEQ ID NO: 2 (c) | CNET adduct (c) |
|---|---|---|---|---|---|---|---|
| 6 (Comparative) | 0.05 | — | — | — | FIG. 9 | 86.53 | 4.39 |
| 7 | 0.05 | 0.03 | 6 | 2 | FIG. 10 | 88.94 | 0.16 |

(a) CT = contact time;
(b) CV = column volumes
(c) % of the total surface of the peak

The invention claimed is:

1. A process for manufacturing an oligonucleotide which comprises removing β-eliminating phosphorus-protecting groups from a protected oligonucleotide attached to a solid support, wherein said removing comprises contacting the protected oligonucleotide in a device having inlet and outlet openings with from 2 to 60 volumes of an amine solution in a solvent which does not consist of pyridine, wherein the conjugate acid of the amine has a pKa greater than 11.5, and wherein the concentration of the amine in the solution is less than 0.5 mole/liters.

2. A process for manufacturing an oligonucleotide which comprises removing β-eliminating phosphorus-protecting groups from a protected oligonucleotide, wherein said removing comprises contacting the protected oligonucleotide with an amine solution in a solvent which does not consist of pyridine, wherein the conjugate acid of the amine has a pKa greater than 11.5, and wherein the concentration of the amine in the solution is from 0.03 to 0.25 mole/liters.

3. The process according to claim 1, wherein the concentration of the amine in the solution is from 0.03 to 0.25 mole/liters.

4. The process according to claim 1, wherein the solvent comprises a halogenated compound or a cyanoalkyl compound.

5. The process according to claim 1, wherein the solvent comprises acetonitrile.

6. The process according to claim 2 wherein the oligonucleotide is contacted with the amine solution for a reaction time from 3 to 360 minutes.

7. The process according to claim 6, wherein the reaction time is less than 30 minutes.

8. The process according to claim 1 wherein the removal is carried out at a temperature from 10° C. to 60° C.

9. The process according to claim 2 wherein the protected oligonucleotide is attached to a solid support.

10. The process according to claim 2 wherein the conjugate acid of the amine has a pKa greater than 11.5 and up to 12.5.

11. The process according to claim 1, wherein the amine is DBU (1,8-Diazabicyclo[5.4.0]undec-7-ene).

12. The process according to claim 2 wherein the total amount of amine which is contacted with the protected oligonucleotide is such that the molar ratio between the amine and the protective groups which are to be removed is equal to or greater than 1.

13. The process according to claim 2 wherein the total amount of amine which is contacted with the protected oligonucleotide is such that the molar ratio between the amine and the protective groups which are to be removed is equal to or greater than 0.01 and equal to or lower than 0.9.

14. The process according to claim 1, wherein the (β-eliminating phosphorus-protecting groups are β-cyanoethyl protective groups.

15. The process according to claim 2, wherein the β-eliminating phosphorus-protecting groups are β-cyanoethyl protective groups.

16. The process according to claim 2, wherein the amine is DBU (1,8-Diazabicyclo[5.4.0]undec-7-ene).

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: Synthetic Sequence

<400> SEQUENCE: 1
tcgtcgtttt gtcgttttgt cgtt                                    24

<210> SEQ ID NO 2
<211> LENGTH: 15
<212> TYPE: DNA
<213> ORGANISM: Artificial
<220> FEATURE:
<223> OTHER INFORMATION: Synthetic sequence
<220> FEATURE:
<221> NAME/KEY: modified_base
<222> LOCATION: (1)..(1)
<223> OTHER INFORMATION: 2'-O,4'-C-methylene-beta-D-ribofuranosyl
      cytosine
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: modified_base
<222> LOCATION: (3)..(3)
<223> OTHER INFORMATION: 2'-O,4'-C-methylene-beta-D-ribofuranosyl
      adenosine
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: modified_base
<222> LOCATION: (6)..(6)
<223> OTHER INFORMATION: 2'-O,4'-C-methylene-beta-D-ribofuranosyl
      guanosine
<220> FEATURE:
<221> NAME/KEY: misc_feature
<222> LOCATION: (6)..(7)
<223> OTHER INFORMATION: n is a, c, g, t or u
<220> FEATURE:
<221> NAME/KEY: modified_base
<222> LOCATION: (7)..(7)
<223> OTHER INFORMATION: 2'-O,4'-C-methylene-beta-D-ribofuranosyl
      thymine
<220> FEATURE:
<221> NAME/KEY: modified_base
<222> LOCATION: (10)..(10)
<223> OTHER INFORMATION: 2'-O,4'-C-methylene-beta-D-ribofuranosyl
      cytosine
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: modified_base
<222> LOCATION: (12)..(12)
<223> OTHER INFORMATION: 2'-O,4'-C-methylene-beta-D-ribofuranosyl
      cytosine
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: modified_base
<222> LOCATION: (14)..(14)
<223> OTHER INFORMATION: 2'-O,4'-C-methylene-beta-D-ribofuranosyl
      cytosine
<220> FEATURE:
<221> NAME/KEY: misc_feature

```
-continued

<222> LOCATION: (14)..(15)
<223> OTHER INFORMATION: n is a, c, g, t or u
<220> FEATURE:
<221> NAME/KEY: modified_base
<222> LOCATION: (15)..(15)
<223> OTHER INFORMATION: 2'-O,4'-C-methylene-beta-D-ribofuranosyl
      cytosine

<400> SEQUENCE: 2
ncnttnncan antnn                                                          15
```